United States Patent
Walton

(10) Patent No.: US 7,679,746 B1
(45) Date of Patent: Mar. 16, 2010

(54) SYSTEM AND METHOD FOR MEASUREMENT OF PRESSURE DROP THROUGH PERFORATED PANELS

(75) Inventor: Steven R. Walton, Buckley, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 12/359,328

(22) Filed: Jan. 25, 2009

(51) Int. Cl.
  *G01N 21/00* (2006.01)

(52) U.S. Cl. .................................... 356/432
(58) Field of Classification Search .......... 356/432
  See application file for complete search history.

(56) References Cited

U.S. PATENT DOCUMENTS 5,210,021 A * 5/1993 Goodwin, Jr. ............... 435/29

* cited by examiner

*Primary Examiner*—Roy Punnoose
(74) *Attorney, Agent, or Firm*—Tung & Associates

(57) ABSTRACT

A system for measurement of pressure drop through a perforated panel having panel holes includes a sensor comprising an illumination source adapted to illuminate the perforated panel, a lens spaced-apart with respect to the illumination source and a camera interfacing with the lens. A controller is connected to the camera and adapted to receive image frames of the panel openings from the camera, measure an optical porosity of the perforated panel, identify a number and locations of missing and blocked panel holes in the perforated panel, determine a shape of a small region associated with each panel hole and calculate a pressure drop through the perforated panel based on the optical porosity of the perforated panel, the number and locations of the missing and blocked panel holes and the shape of the small region associated with each panel hole.

22 Claims, 11 Drawing Sheets

RAW-IMAGE

DEFINITIONS

SYSTEM AND METHOD FOR MEASUREMENT OF PRESSURE DROP THROUGH PERFORATED PANELS

TECHNICAL FIELD

The present disclosure relates to measurement of pressure drop through perforated panels. More particularly, the present disclosure relates to a system and method which can be used to measure drop in pressure through drilled perforated panels by determining the optical porosity of the panels.

BACKGROUND

One approach to drag reduction in aircraft, which can lead to significant fuel savings, includes modification of the laminar airflow across an airfoil surface by making it porous and applying a controlled vacuum from within the airfoil body. Airflow through the panels which form the airfoil surface may occur through thousands or millions of tiny holes, each only a few thousandths of an inch in diameter, which may be "drilled" in the panel using a high-power pulsed laser beam. The holes may be distributed around the surface of the panel in a pattern with a density that is determined by the aerodynamic design.

In order to achieve the expected drag reduction of an airfoil surface, it may be necessary to ensure that the manufacture of porous airfoil surfaces be accomplished within specific tolerances, expressed in terms of pressure drop (Pd) across the panel, and that the relative designed geometry of regions of varying Pd be rigidly controlled to this end. However, the available methods of measuring pressure drop through the panel may be cumbersome, slow, and require painstaking care to achieve the required accuracy.

Optical porosity seeks to establish a correlation between Pd and the amount of light that can be transmitted through an hole or holes in a panel using a backlight and some form of light sensor. In the paper "Light transmission control technique and correlation with pressure loss characteristics of perforated panels for Hybrid Laminar Flow Applications" presented by B. Paluch at the *Proceedings of the CRAS/DragNet European Drag Reduction Conference,* 19-21 Jun. 2000, in Potsdam, Germany, it was established that there is a high correlation (0.956 in the test configuration described) between total air flow through a test panel and the optical power transmitted through its perforations from a halogen point light source.

Results from shape analysis experimentation suggest that the feature of an hole in a panel that is most strongly correlated with pressure drop through the panel is simply the area of the hole. Research into laminar flow reduction suggests that the geometry of distribution of the holes within a panel may be an important factor which determines drag reduction performance, and the locations of completely plugged holes in the panel may have a significant effect.

Therefore, an expeditious and efficient method of inspecting large areas of a perforated panel which utilizes optical porosity of the panel to determine pressure drop through the panel is needed.

SUMMARY

The present disclosure is generally directed to a system for measurement of pressure drop through a perforated panel having panel holes. An illustrative embodiment of the system includes a sensor comprising an illumination source adapted to illuminate the perforated panel, a lens spaced-apart with respect to the illumination source and a camera interfacing with the lens. A controller is connected to the camera and adapted to receive image frames of the panel openings from the camera, measure an optical porosity of the perforated panel, identify a number and locations of missing and blocked panel holes in the perforated panel, determine a shape of a small region associated with each panel hole and calculate a pressure drop through the perforated panel based on the optical porosity of the perforated panel, the number and locations of the missing and blocked panel holes and the shape of the small region associated with each panel hole.

The present disclosure is further generally directed to method for measurement of pressure drop through a perforated panel having panel holes. An illustrative embodiment of the method includes loading a perforated panel having panel holes, executing a scan of the perforated panel by illuminating the perforated panel and capturing image frames of the panel holes in the perforated panel and summarizing and archiving data by measuring an optical porosity of the perforated panel, identifying a number and locations of missing and blocked panel holes in the perforated panel and calculating a pressure drop through the perforated panel based on the optical porosity of the perforated panel and the number and locations of missing and blocked panel holes in the perforated panel.

In some embodiments, the method may include loading a perforated panel into position for imaging; illuminating the perforated panel; capturing images of panel holes in the perforated panel; pre-processing the images; extracting metageometry of the panel holes; assembling image statistics based on the metageometry; determining a pressure drop through the perforated panel based on the image statistics; and formatting display data of the pressure drop.

In some embodiments, the system for measurement of a pressure drop through a perforated panel may include a sensor adapted for moving in a scanning motion relative to the perforated panel and comprising a distributed light illumination source such as an illuminated plate or fluorescent panel adapted to backlight the perforated panel, a telecentric lens spaced-apart with respect to the illumination source and a camera interfacing with the lens; and a controller connected to the camera and adapted to receive image frames of the panel openings from the camera, the controller comprising a blob detection component adapted to find locations of the panel holes in the perforated panel and use grayscale information to measure total optical power of light rays transmitted from the illumination source through the perforated panel; an optical porosity measurement component adapted to measure optical porosity by summing a pixel response in the local region of each of the panel holes; an image frame analyzing component adapted to analyze individual image frames from the camera and identify spacing and expected locations of the panel holes in the perforated panel; a small region measurement component adapted to utilize spacing and expected locations of the panel holes and measure the shape of a small region associated with each panel hole; and a pressure drop calculating component adapted to calculate and display a pressure drop over the perforated panel.

In some embodiments, the method may include loading a perforated panel into position for imaging; backlighting the perforated panel with light rays from an illumination source; capturing images of panel holes in the perforated panel; pre-processing the images by acquiring the images, normalizing the images and updating camera controls and extracting a list of blobs; extracting metageometry of the panel holes by obtaining a first approximation of hole spacing, identifying and measuring an angle of a scanning axis, identifying pulse spacing of panel openings along the scanning axis, locating a probable location of plugged holes in the perforated panel, constructing a semantic representation of an array of the panel holes in the perforated panel, identifying hole-local regions and measuring a total optical power of each panel hole; assembling image statistics based on the metageometry by obtaining a Y-axis servo hunting magnitude and variation, obtaining a spacing magnitude and variation along the scanning direction, obtaining an interline spacing of the panel holes, obtaining an optical porosity of the perforated panel per unit area, obtaining a variance of optical porosity within the images, obtaining a percentage of blocked panel openings in the perforated panel and obtaining a scanning angle; determining a pressure drop through the perforated panel based on the image statistics; and formatting display data of the pressure drop.

BRIEF DESCRIPTION OF THE ILLUSTRATIONS

DETAILED DESCRIPTION

Figure 1:
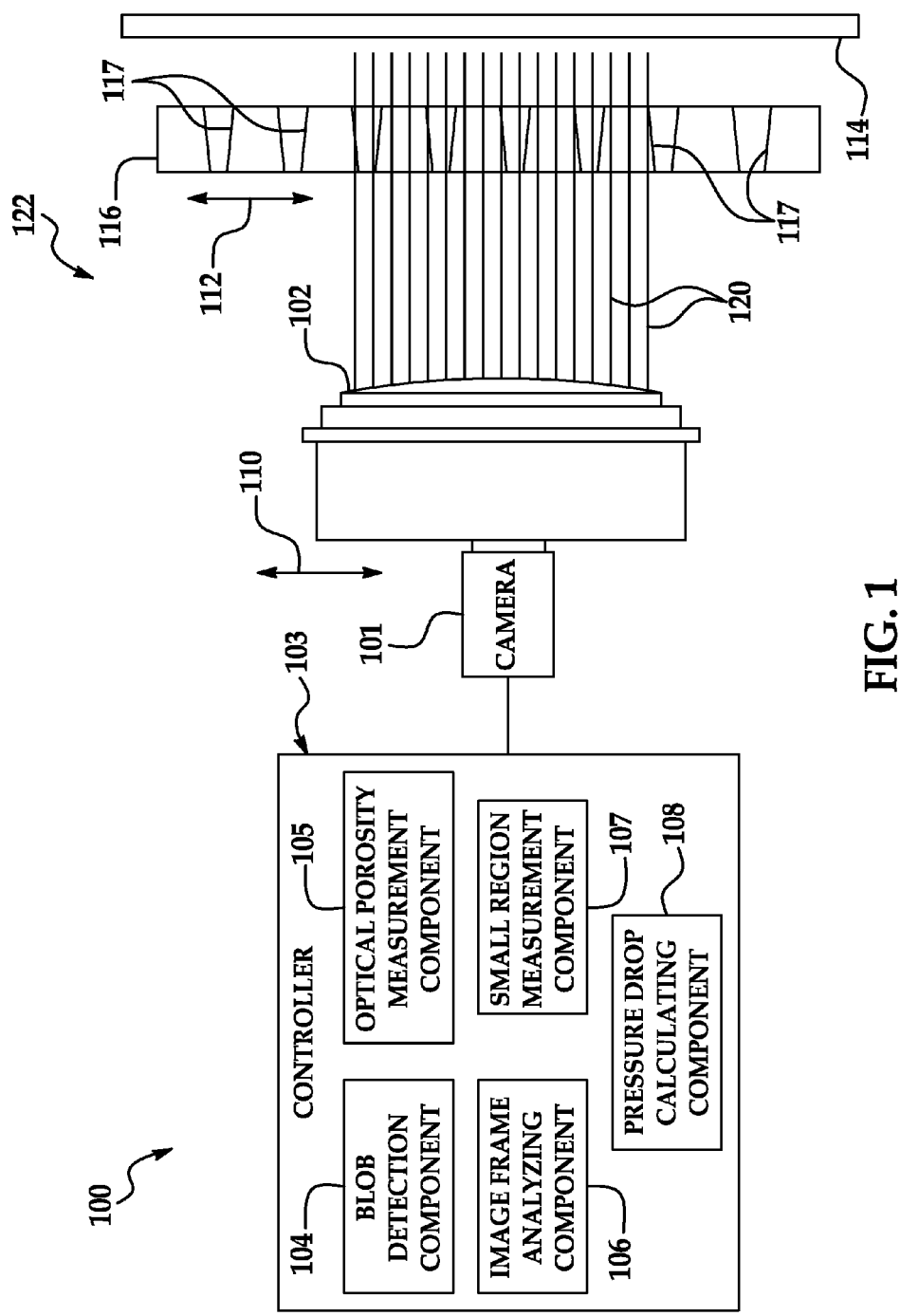
FIG. 1 is a block diagram which illustrates an illustrative embodiment of a system for measurement of pressure drop through perforated panels.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the invention and are not intended to limit the scope of the invention, which is defined by the claims. Furthermore, there is no intention to be bound by any expressed or implied theory presented in the preceding technical field, background, brief summary or the following detailed description.

The present disclosure is generally directed to a method of inspecting large areas of a perforated panel and utilizing optical porosity of the panel to determine pressure drop (Pd) through the panel. The method may include determining the density and distribution of plugged holes even as the geometric nature of the designed hole distribution may change across the panel surface. Since this geometry can be a constantly-changing function of location, the method may independently determine the orientation and hole pattern geometry directly from each image without the use of any reference standards. The array of bright dots which represent the hole pattern may be turned into a semantic representation of lines, orientations, and spacings from which one can directly calculate the associated Pd per unit area and geometric conformance to design standards.

Referring to the drawings, an illustrative embodiment of a system which is suitable for measurement of pressure drop perforated panels, hereinafter system, is generally indicated by reference numeral 100 in FIG. 1. The system 100 may include a camera 101 which may be a high-resolution machine vision area digital camera, for example and without limitation. The camera 101 may interface with a lens 102, which in some embodiments may be a telecentric lens. The lens 102 may be adapted to parallelize light rays 120 which are emitted from a suitable illumination source 114. The illumination source may be a flat distributed light source, for example and without limitation. In implementation of the system 100, which will be hereinafter described, a perforated panel 116, through which extends panel holes 117, may be positioned between the illumination source 114 and the telecentric lens 102. In some applications, hundreds of the panel holes 117 may be located in each image frame of the camera 101. The illumination source 114 may be adapted to backlight the perforated panel 116 to determine the optical porosity of the perforated panel 116. The optical porosity of the perforated panel 116 may indicate the drop in pressure (Pd) through the perforated panel 116. Use of a telecentric lens 102 may enable coverage of a wider FOV of the perforated panel 116 without perspective distortion.

In some embodiments of the system 100, the camera 101 and the lens 102, along with the illumination source 114 (hereinafter sensor 122), may be adapted to scan along the perforated panel 116, which may remain stationary, as indicated by the arrow 110. In other embodiments of the system 100' the perforated panel 116 may be adapted to move, as indicated by the arrow 112, while the sensor 122 (which includes the camera 101, the lens 102 and the illumination source 114) may remain stationary during scanning of the perforated panel 116. In still other embodiments, scanning may be accomplished by a combination of movement of the sensor 122 and the perforated panel 116.

A controller 103 may interface with the camera 101. The controller 103 may include a blob detection component 104, an optical porosity measurement component 105, an image frame analyzing component 106, a small region measurement component 107 and a pressure drop calculating component 108. The blob detection component 104 may be adapted to quickly find locations of the panel holes 117 in the perforated panel 116 and use grayscale information to measure total optical power of the light rays 120 transmitted through the perforated panel 116. The optical porosity measurement component 105 may be adapted to measure optical porosity by summing the pixel response in the local region of each panel hole 117. The image frame analyzing component 106 may be adapted to analyze individual image frames from the camera 101 in order to identify the spacing and expected locations of panel holes 117 in the perforated panel 116. The spacing and expected locations of the panel holes 117 may then be used to identify missing or blocked panel holes 117 in the perforated panel 116. The small region measurement component 107 may be adapted to utilize spacing and expected locations of the panel holes 117 to measure the shape of the small region associated with each panel hole 117. This may allow determination of the exact contribution of each individual open panel hole 117 to the corresponding micro-regional area of the panel hole 117, thus eliminating aliasing artifacts. The pressure drop calculating component 108 may be adapted to calculate and display in real time the pressure drop over the entire perforated panel 116 in an easily-assimilated form, which may include the automatic detection of defective hole regions of any size, for an operator (not shown) of the system 100.

In typical operation of the system 100, which will be hereinafter further described, a perforated panel 116, through which extends panel holes 117, may be placed between the lens 102 and the illumination source 114 of the sensor 122. The illumination source 114 emits light rays 120 through the panel holes 117 in the perforated panel 116. The lens 102 may parallelize the light rays 120. Simultaneously, the camera 101 and the lens 102, along with the illumination source 114 of the sensor 122, may be moved in a scanning motion, as indicated by the arrow 110, while the perforated panel 116 may remain stationary. Alternatively, the perforated panel 116 may move in a scanning motion, as indicated by the arrow 112, while the sensor 122 remains stationary. Still further in the alternative, both the sensor 122 and the perforated panel 116 may move during the scan.

The camera 101 may capture images of multiple panel holes 117 in the perforated panel 116 in each image frame. The blob detection component 104 of the controller 103 may quickly find locations of the panel holes 117 in each image frame and may subsequently use grayscale information in the hole locations to measure the total optical power which is transmitted through the panel holes 117. The optical porosity measurement component 105 may measure the optical porosity of the perforated panel 116 by summing the pixel response in the local region of each panel hole 117. The image frame analyzing component 106 may analyze the individual image frames of the camera 101 so as to identify the spacing and expected locations of panel holes 117 in the perforated panel 116. The image frame analyzing component 106 may utilize the spacing and expected locations of the panel holes 117 to identify missing or blocked panel holes 117. The small region measurement component 107 may utilize the spacing and expected locations of the panel holes 117 to measure the exact shape of the small region associated with each panel hole 117, thus allowing the exact contribution of each individual open panel hole 117 to the corresponding micro-regional area and thus eliminating all aliasing artifacts. The pressure drop calculating component 108 may then calculate and display in real time the pressure drop (Pd) over the entire perforated panel 116. The display may be presented in an easily-assimilated form and may include the automatic detection of defective regions of any size.

Figure 2:
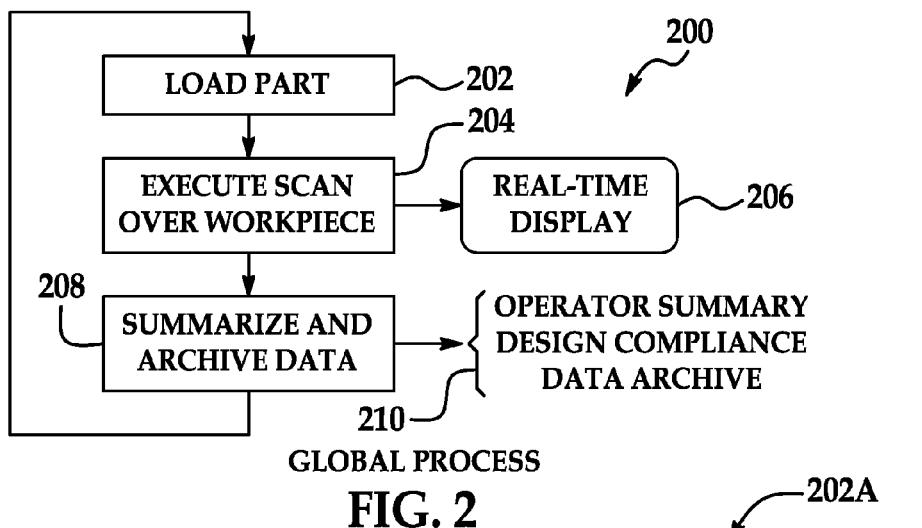
FIG. 2 is a flow diagram which summarizes an illustrative embodiment of a method for measurement of pressure drop through perforated panels.

In FIG. 2, a flow diagram 200 which summarizes an illustrative embodiment of a method for measurement of pressure drop through perforated panels, hereinafter method, using the system 100 in FIG. 1 is shown. In block 202, the perforated panel 116 may be loaded into position between the lens 102 and the illumination source 114. In block 204, the perforated panel 116 or the sensor 122 may be moved through a programmed scan as the light rays 120 from the illumination source 114 are emitted through the perforated panel 116 to the lens 102. Throughout the scan, the controller 103 may monitor the results of the scan in real time. After the controller 103 assembles and reports the resulting data, the perforated panel 116 may be removed from between the lens 102 and the illumination source 114. The controller 103 may flag nonconformance to design specifications and report the resulting data to archived data storage.

Figure 3:
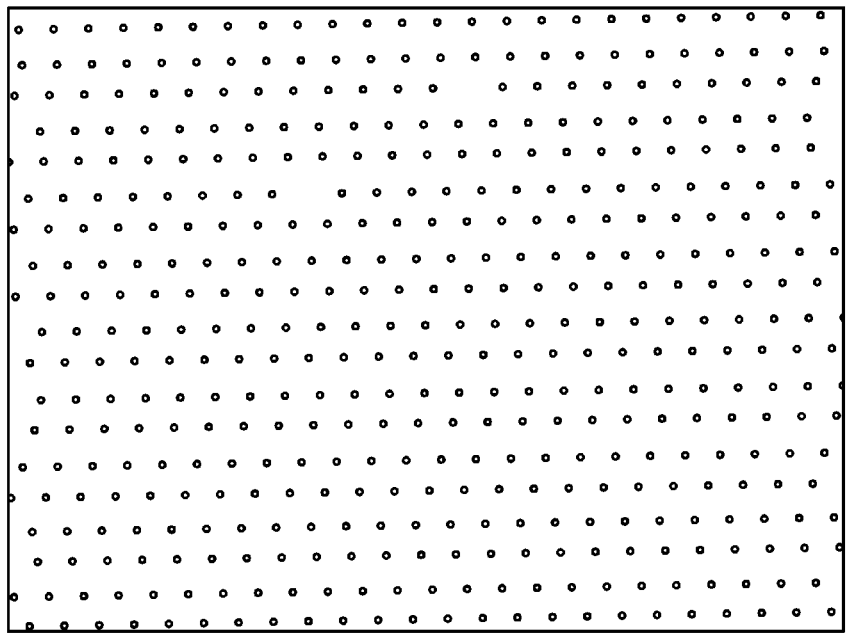
FIG. 3 is reproduction of an image of a perforated panel.

FIG. 3 is reproduction of an image of a perforated panel which may be imaged by the camera 101. In the image of FIG. 3, several of the panel holes, evenly distributed around the imager are plugged.

Figure 4:
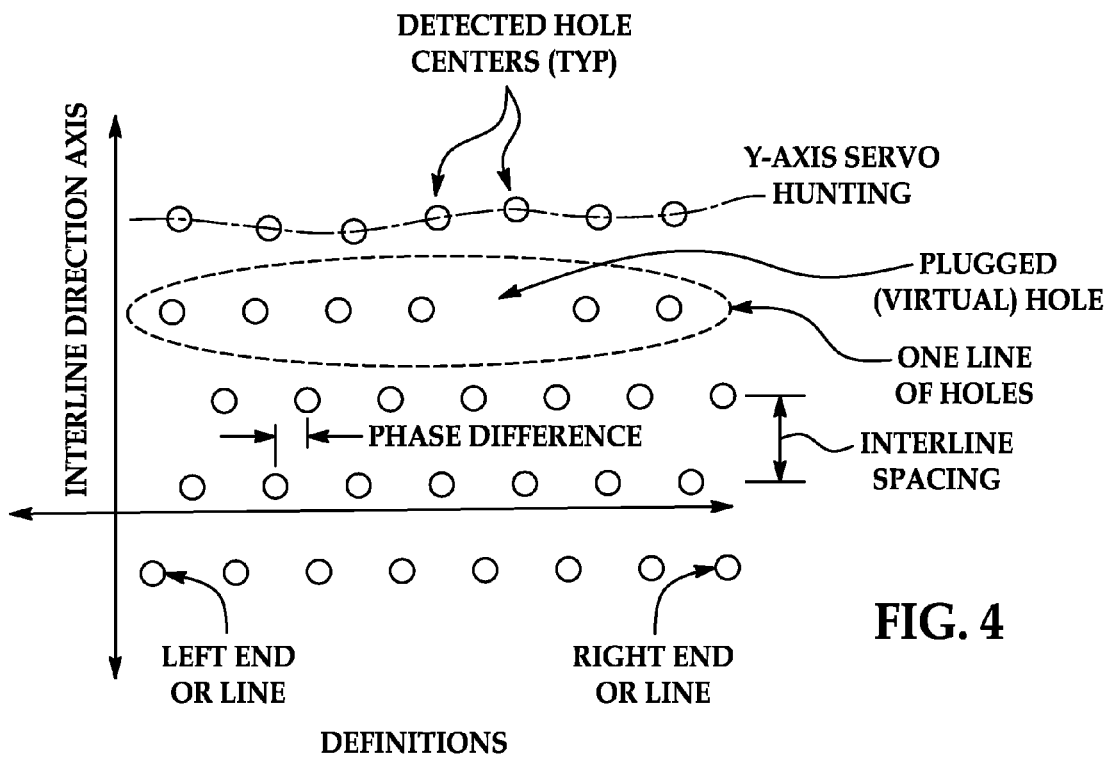
FIG. 4 is a schematic diagram which illustrates interpretation of a typical image frame captured by a sensor camera in implementation of an illustrative embodiment of the system and method for measurement of pressure drop through perforated panels.

The method 200 (FIG. 2) may utilize realtime analysis of each image frame acquired by the camera 101 during scanning. FIG. 4 illustrates how a typical image frame as captured by a sensor camera 101 is interpreted. Perforations or panel holes are shown in the figure as circles, with their locations marked with small crosshairs. Due to the nature of the manufacturing process by which the perforated panel 116 may be produced, panel holes may be drilled by moving a pulsed high-energy laser along a scanning direction, or scanning axis. This scanning direction or axis may not align with the image frame of the camera 101. Lines may be stacked up beside each other by moving the laser sideways at some interline spacing and repeating a line, but without control over whether the panel holes of one line are immediately adjacent to the panel holes of the neighbor, leading to a phase difference between lines. One "line of holes" is simply all of the holes that appear within the width of an image, with the understanding that the line continues beyond either side of the image and will be measured by subsequent images when the gantry or part has moved. Some panel holes may be plugged or missing. The location of these panel holes (virtual holes) may be determined by a best-estimate driven by semantic algorithms. Finally, it may be necessary to identify which holes are at the ends of each line (within the image). This information may be used to determine the spacing of panel holes within a line even in the presence of one or more virtual holes.

Conventional methods may be very difficult to use for this problem because each row of holes within an image may vary in phase position relative to its neighboring rows, because the servo-hunting means that holes aren't precisely on a line, and because plugged (missing) holes can drastically alter the perceived geometry. Therefore, it may be necessary to identify and measure of all these characteristics for any given image, despite these variations.

As used herein, an image as captured by the camera 101 of the sensor 122 may include an array of bytes (numbers that range from 0 to 255) representing optical brightness of two-dimension positions (pixels) in a focused image, arranged in rows and columns. An image may include no information as to what objects appear within it, other than their appearance in two dimensions. A blob (shorthand for "binary large object") may be the first step in extracting some semantic meaning from these numbers, and may include a local group of bright pixels—in this case, the bright light coming through a given panel hole. Instead of a simple array of numbers, common in programming, all the blobs in an image may be identified as members of a list. The members of this list may be organized in any order, but each list element representing an individual blob may contain at a minimum its location (row and column in the image) and its size (number of connected pixels). Subsequently, additional semantic characteristics may be added to the blobs as determinations are made about their nature as holes, which may include characteristics such as total brightness; shape; membership in a given line; whether a hole is at the left end or right end of its line; whether the hole represents a virtual hole; and the amount of non-perforated panel surface area that surrounds the hole. Each frame of data may include lines of holes which may be blobs formed of pixels in an image. Only the image pixels may be a simple numeric data type.

Figure 2A:
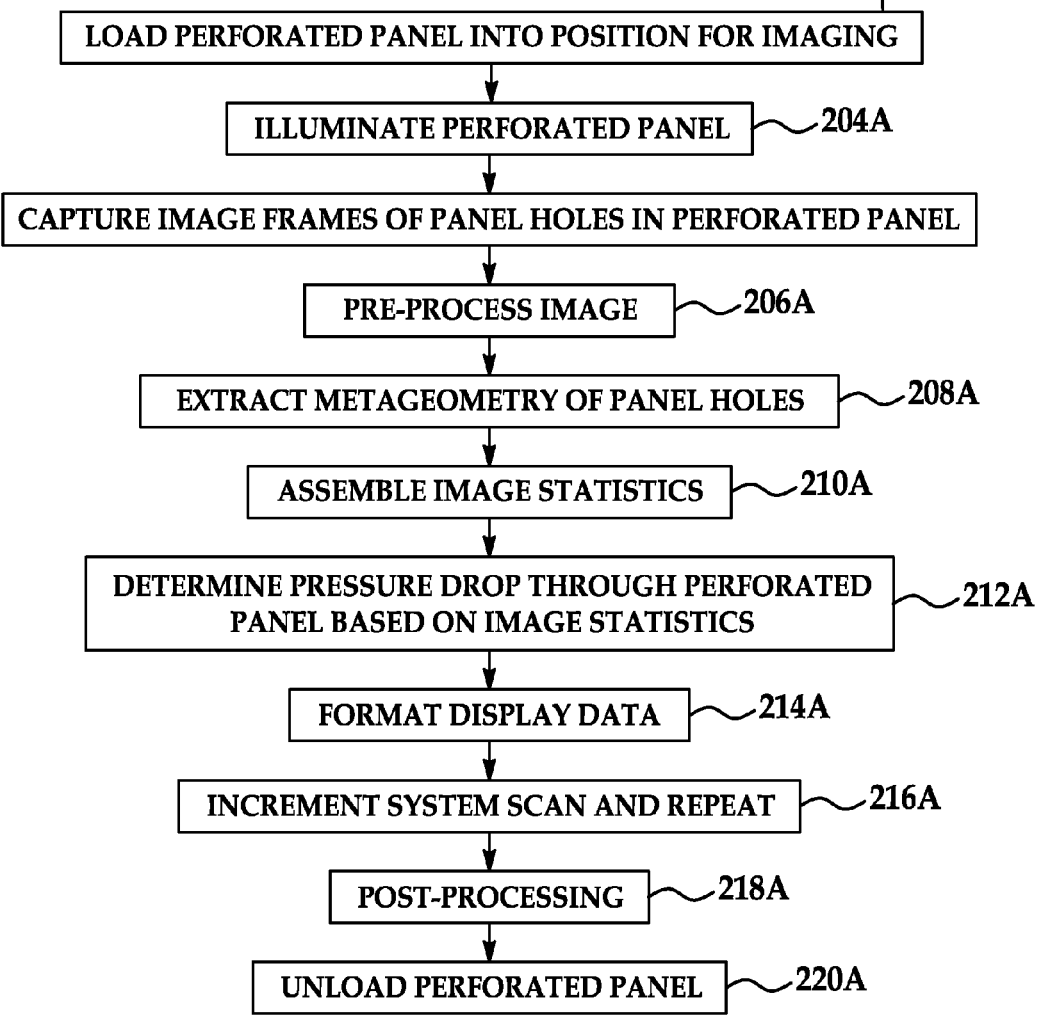
FIG. 2A is a flow diagram which details an illustrative embodiment of a method for measurement of pressure drop through perforated panels.

As shown by the flow diagram 200*a* in FIG. 2A, in more detail, the method 200 may include the following:

Block 202*a*. Load perforated panel 116 into position for imaging;

Block 204*a*. Illuminate perforated panel 116 with light rays 120 from illumination source 114;

Block 206*a*. Capture image frames of panel holes 117 in perforated panel 116;

Block 208*a*. Pre-process image
  Acquire Image;
  Normalize image and update camera controls;
  Extract a list of blobs;

Block 210*a*. Extract metageometry
  First approximation of hole spacing;
  Identify and measure the angle of the scanning axis;
  Identify pulse spacing along scanning axis;
  Locate probable location of plugged (virtual) holes;
  Construct semantic representation of hole array;
  Identify hole-local regions ("cells");
  Measure total optical power of each hole;

Block 212*a*. Assemble image statistics based on metageomatry
  Y-axis servo hunting magnitude and variation;
  Spacing magnitude and variation along scanning direction;
  Interline spacing;
  Optical porosity per unit area (relates to Pd);
  Variance of optical porosity within image;
  Percentage of blocked holes;
  Scanning direction (angle);

Block 212*b*. Determine pressure drop through perforated panel based on image statistics Block 214*a*. Format and display pressure drop data for Operator;

Block 216*a*. Increment sensor scan position and repeat steps 2-5 until finished;

Block 218*a*. Post-processing
  a Correlate (map) individual image statistics to part geometry;
  Create and display computer graphic image of part with Pd (pressure drop) indication;
  Identify and display regional specification compliance;
  Record relevant information for future reference and/or documentation; and Block 220*a*. Unload perforated panel 116 from system 100

Loading and Imaging

Scanning of the perforated panel 116 may be accomplished in several ways, and the exact method of loading a perforated panel 116 into the system 100 may depend on which method is used. For instance, the so-called "step-and-repeat" method, wherewith the sensor 122 or panel 116 is moved to the each test location and halts for images to be triggered while the panel 116 and sensor 122 are stationary with respect to each other, may require the use of an expensive moving gantry to hold the sensor 122 or panel 116. A pre-programmed path may move the measurement field around the panel 116 until it has been completely inspected.

Figure 5A:
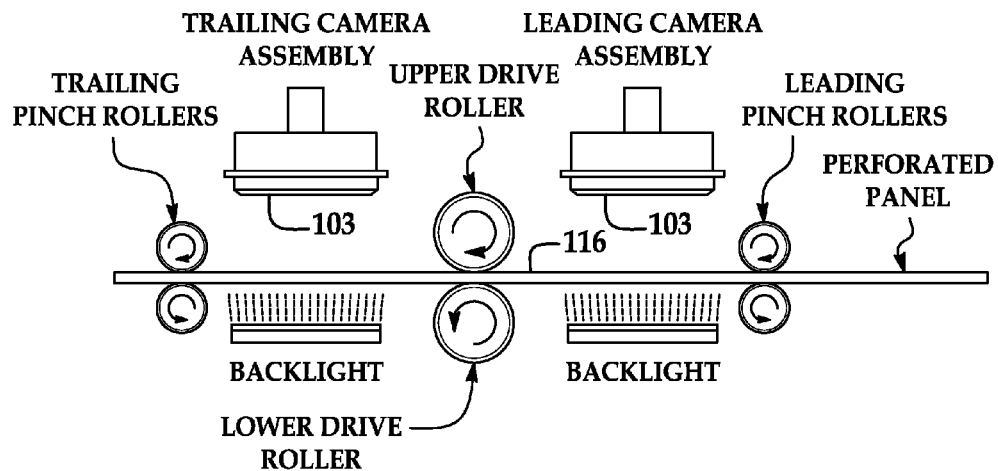
FIG. 5A is a top view which illustrates a combination of a moving perforated panel and a row of stationary cameras that film the panel in implementation of an illustrative embodiment of the system and method for measurement of pressure drop through perforated panels.
Figure 5B:
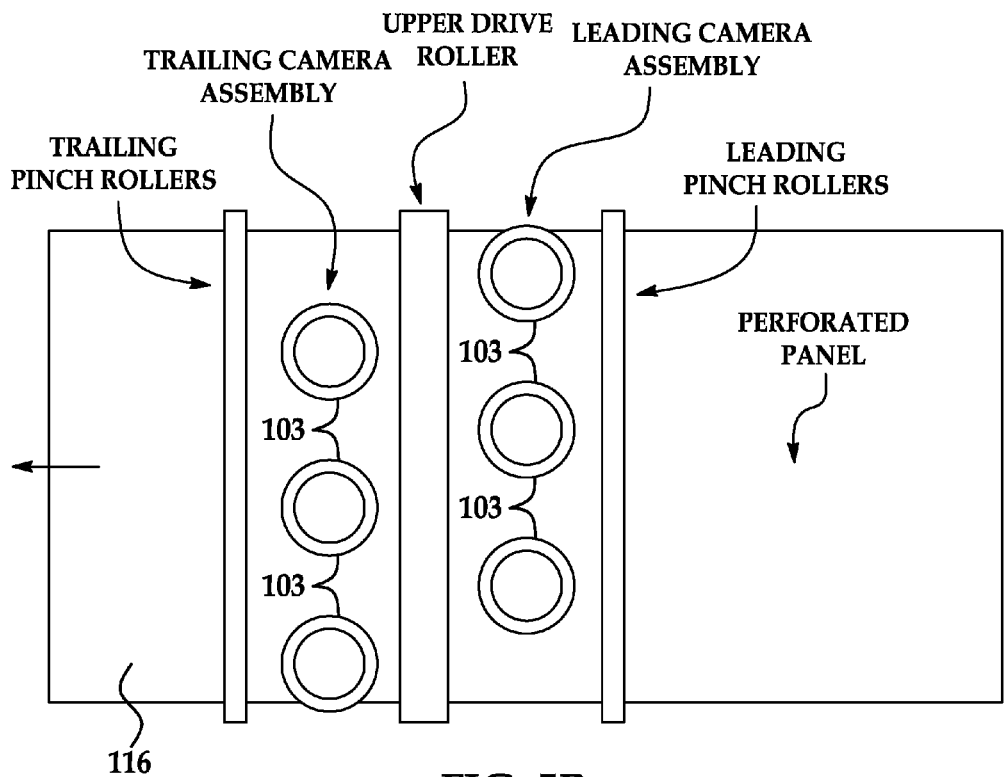
FIG. 5B is a side view of the moving perforated panel and stationary cameras shown in FIG. 5A.

Alternatively, if the sensor 122 has been designed with sufficient optical gain and the backlight from the illumination source 114 is sufficiently bright, the panel 116 may be imaged while it is moving. The latter technique is faster in practice and may be implemented in many different ways. One method, which may be built to deploy the system 100, is a combination of a moving part and a row of stationary cameras 103 that cover the width of the perforated panel 116 is used, as shown in FIGS. 5A and 5B. Two rows of cameras 103 may be positioned in such a way as to obtain 100% coverage of the surface of the perforated panel 116, as illustrated.

Pre-Processing Image

Figure 6:
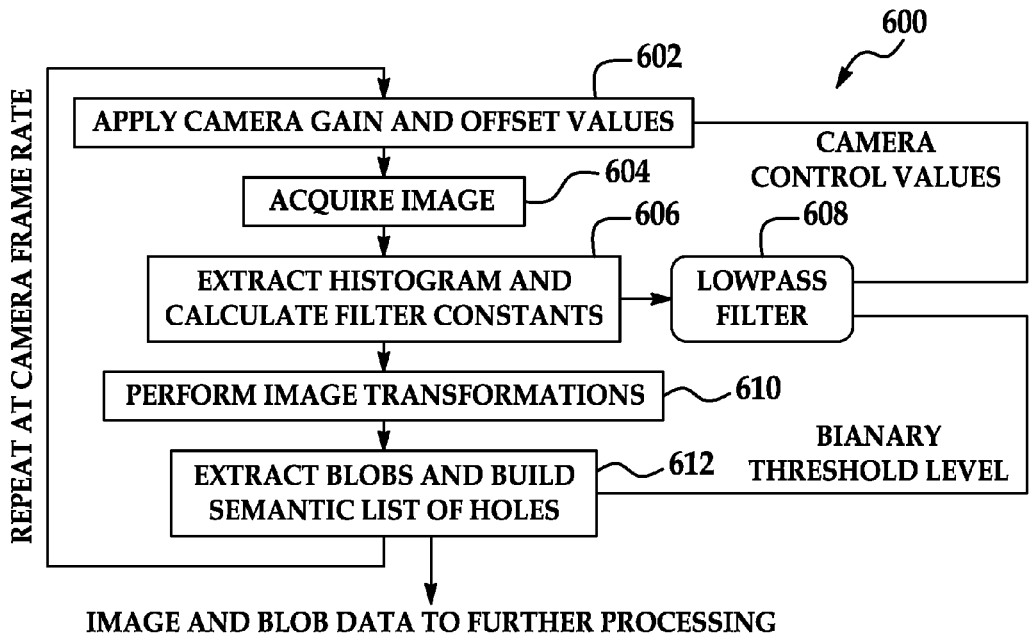
FIG. 6 is a flow diagram which illustrates pre-processing of a panel image in implementation of an illustrative embodiment of the system and method for measurement of pressure drop through perforated panels.

Pre-processing of the image captured by the camera 103 may be accomplished as shown in the flow diagram 600 shown in FIG. 6. In block 602, the camera gain and DC offset (black level) may be set, according to the output of a lowpass filter, replacing the camera's built-in AGC. These control signals may come from a filter with a large time constant so that large changes of background appearance due to changes in area lighting level or surface reflectivity may be accounted for. (The signal levels involved in this calibration may be made available to an executive portion so that the administrating process may determine sensor image validity, e.g., to make an independent evaluation of whether a given image frame is actually viewing a valid workpiece).

In block 604, the next image may be acquired as it becomes available, such as through an appropriate physical transport mechanism, e.g. a digital camera 101 and its associated communication bus. The camera 101 may be operated with a disabled automatic gain control (AGC) because the nature of the images may disrupt the manner in which the circuits are normally designed. AGC may be done in software according to algorithms mentioned herein.

In block 606, a full-image power histogram may be extracted and the probable mean intensity (brightness) of the background surface and of the panel holes 117 may be located. Correction signals to the camera DC offset and gain may be calculated to move the background power level into the lower 25% of the histogram and push the larger power level coming through the perforations into the upper 75%. The gain and offset filter inputs may be updated with these corrections.

In block 610, any geometric image warping or mapping (e.g., rotating it by 90 degrees) that is required by the physical mounting orientation of the camera sensor 122 may be applied in software. The correct goal is one in which the scanning direction of the panel holes 117 is within plus or minus 45 degrees of the horizontal orientation of the image frame.

In block 612, a list of blobs may be extracted according to a binary threshold related to custom AGC algorithms. This may be the first place where the nature of the signal processing moves from a two-dimensional image representation into a semantic list of data objects, in this case the size and location of discrete bright spots representing the panel holes 117.

Extracting Metageometry

This task may create an understanding of the lines of panel holes 117 along the scanning direction, which may vary through a wide range of angles, as they are visible within the image frame. A certain percentage of these panel holes 117 may be plugged and thus be invisible to the camera 101. Since this semantic abstraction relies on the underlying geometry, the term "metageometry" may be used to describe it.

The two main levels of abstraction are holes and lines. The list of blobs becomes a list of holes when the characteristics of sizes optical power, and line membership are ascribed to their descriptions by various algorithms. Holes become elements in a list of lines that may be produced when it is discovered which holes are the right and left ends, and which holes lie close to a line between them. Parameters such as y-axis servo wander may be added by other algorithms to each line object. The line list may then be used to discover the location of virtual holes, the spacing between lines, and the size of the local regions around each hole. These last characteristics may be used to generate the basic characteristics of the perforated panel that the system was designed to measure: optical porosity per unit area, percentage of plugged holes, and basic geometric compliance to design specifications with regard to hole spacing, array shape, and two dimensional distribution across the part.

Figure 7:
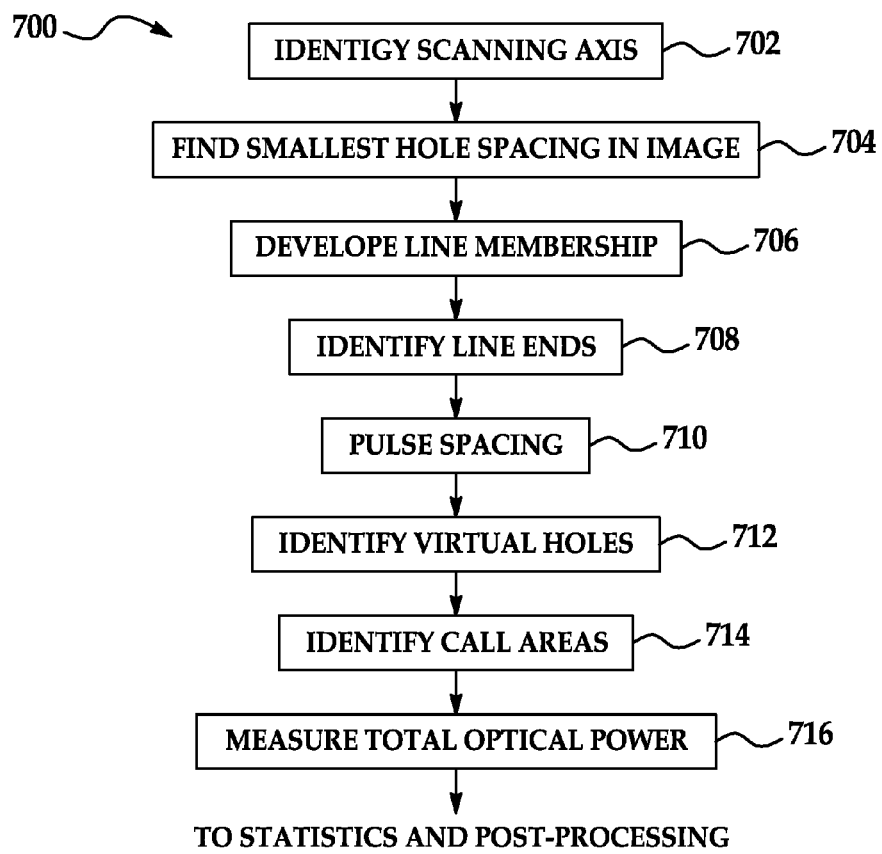
FIG. 7 is a flow diagram which illustrates a metageometry extraction process in implementation of an illustrative embodiment of the system and method for measurement of pressure drop through perforated panels.

The flow diagram 700 shown in FIG. 7 illustrates a metageometry extraction process in implementation of an illustrative embodiment of the system and method.

Scanning Axis Identification

Figure 8A:
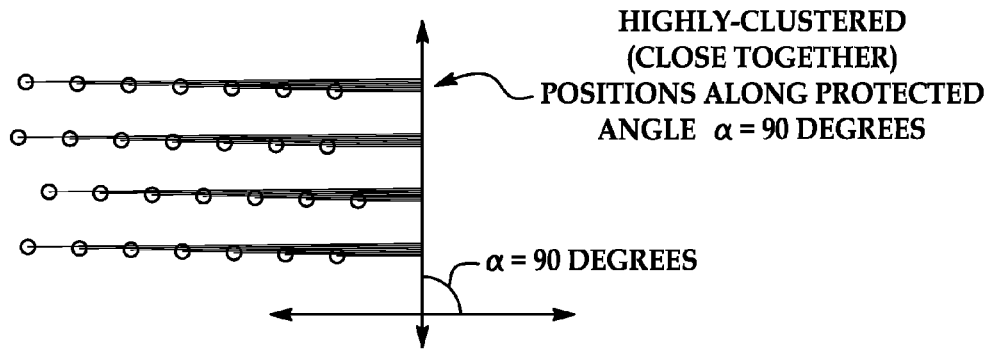
FIG. 8A is a line graph which illustrates a method of developing line membership of an hole in a highly-clustered pattern of holes in a perforated panel.
Figure 8B:
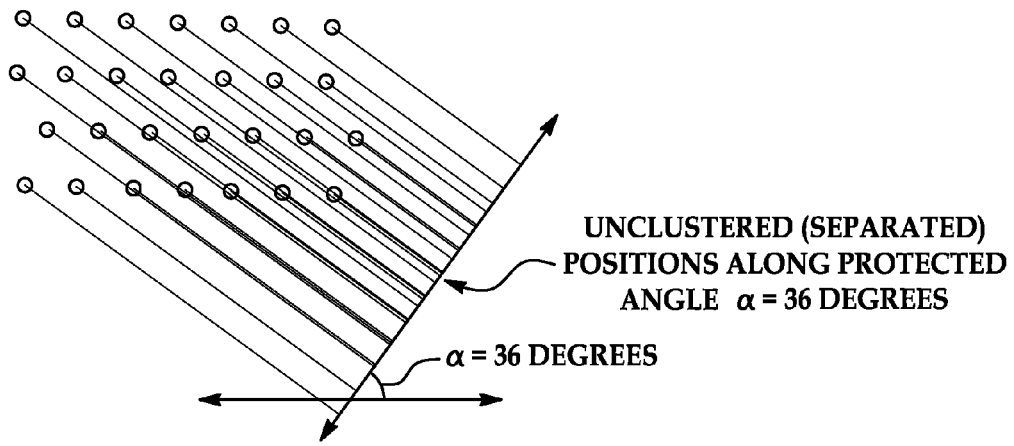
FIG. 8B is a line graph which illustrates a method of developing line membership of an hole in a non-clustered pattern of holes in a perforated panel.

In block 702, after a fresh image and a list of blobs is obtained, the first task may include identification of the scanning axis direction, which may later be used to discover the locations of lines of holes. FIGS. 8A and 8B illustrate how this may be accomplished. In FIG. 8A, it is noted that due to the basic nature of straight lines of holes, the locations along some line of projection at angle α from horizontal will form tight clusters when this line is nearly perpendicular to the scanning axis direction, as shown. In contrast, when the angle α is not near perpendicular, as seen in FIG. 8B, where α is 36 degrees, the locations may be loosely clustered or not clustered at all.

This clustering behavior may be used by modeling the locations along the line of projection as though they were particles exerting a force among themselves proportional to some power factor of their separation. The total "force" contained in the population can be found by the equation at the bottom of FIG. 8B. Thus, to find the angle of the scanning direction, angle α is simply driven through 180 degrees while the "force" and look for a peak is calculated. Since α represents a perpendicular projection, the scanning axis angle is simply 90 degrees away from it.

One important characteristic of this model is that the "force" may be a continuous function of angle α, with infinite resolution. Thus, it may be possible to perturbate around the candidate peak location to find the exact scanning angle to any desired resolution. Other methods for solving this kind of problem tend to apply a binning procedure, which may be limited in resolution to the size of the bins and thus may not achieve the precision which the method 200 exhibits.

Nearest Neighbor

In block 704, the minimum distance between any two holes in the image may be used below in identifying lines. It is found simply by going through the entire list of blobs and determining the Euclidean distance between each pair. Out of all possible pairs, the shortest distance may be kept. This value is referred to as the nearest neighbor distance herein. Additionally, the average neighbor distance may be measured, which may be used later in limited the search range of the filtering process used to measure spacing along the lines of holes.

Develop Line Membership

An image frame may contain one or more lines, up to several dozen depending upon how the camera field of view has been set up and what the designed hole spacing is for the particular part being inspected. Two different methods may be used to determine so-called line membership for each hole in the image in block 706 of FIG. 7. This is a characteristic that is added to each member of the hole list. The results of these two independent methods may be compared to each other to increase confidence that a correct assessment has been made.

Figure 9:
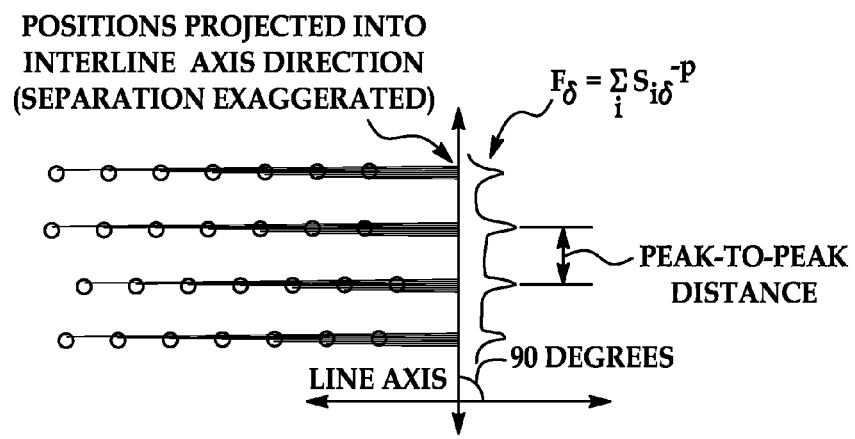
FIG. 9 is a line graph which illustrates another method of developing line membership of an hole in a pattern of holes in a perforated panel.

First, a method similar to that used to find the scanning direction angle α may be used to create a function along the perpendicular (interline) direction that has peaks near the locations of lines. FIG. 9 depicts this method graphically. The peaks are simply numbered sequentially from one, and peak membership (similar to line membership) is added to each hole as this numerical value. The projected location onto the interline direction axis of each hole in the entire population is compared to these peak locations, and any location within half of the nearest neighbor distance of a peak is given the number of that peak. If a given hole does not fall within this distance of any peak, it is called an orphan and given a peak membership value of zero. Note that this method allows simply scanning through the total list of holes in order from first to last, because each hole is assigned a peak membership immediately, independent of any other hole. Lines as manipulable semantic entities in themselves are not developed.

Figure 10:
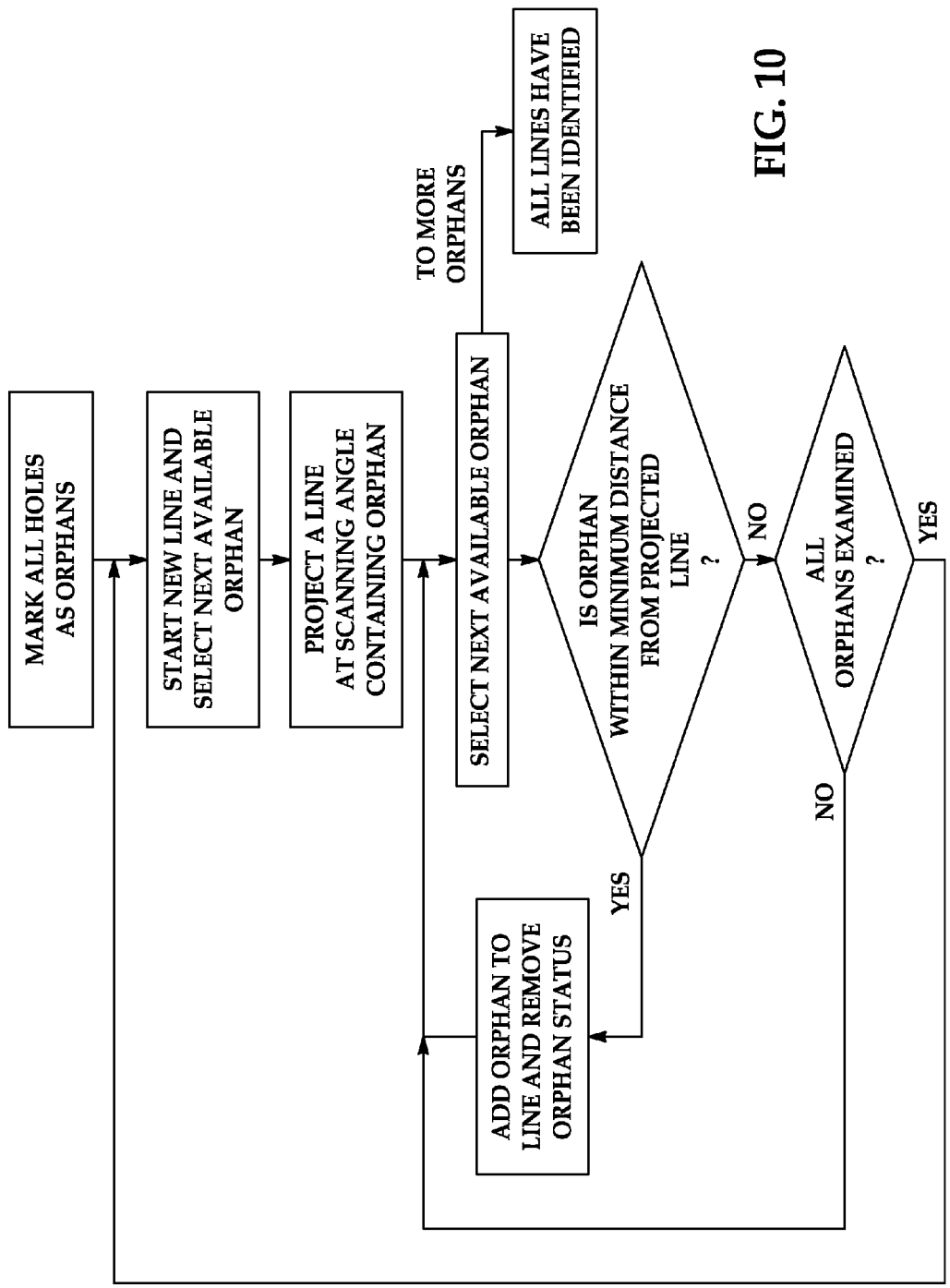
FIG. 10 is a line graph which illustrates building of a list of lines consisting of related holes in developing line membership of an hole.

The second method is conceptually very similar, but actually builds a list of lines consisting of related holes. A given line is discovered, then fully populated before moving ahead to the next line. Thus by the time the process is complete a list of manipulable semantic entities has been populated. This is a snapshot of the image frame as a list of distinct lines of perforations. FIG. 10 is a flow chart which illustrates this method. All holes in the image are assigned an orphan status, where the line membership value is set to zero. Then, any orphan hole is selected from the population and an imaginary line drawn from it at the scanning angle α, a new candidate line entity in a list is established. The rest of the population of orphans may then be scanned. If a hole is within the nearest neighbor distance of this line, the numerical value of the current line may be assigned to it (replacing the orphan status value of zero), and it may be added to the list of holes being collected under the current line. If no more orphan holes are within nearest neighbor distance of the current line, then a new line may be started by the next available orphan. This process may be repeated until no additional lines can be created.

At this point, the list of lines is traversed, one line at a time, to ensure that all of the holes in any given line share the same peak membership that was found earlier, as described above. Any holes that do not may be returned to orphan status and treated separated or ignored later on.

Identify Line Ends

In block 708, the abstract semantic list of lines, wherein each line is an unordered list of holes, may be used to easily determine the left-most and right-most hole for each line. This may be done by traversing the list and keeping track of the minimum and maximum horizontal locations of the holes (the geometry is rotated such that the scanning direction is aligned with the horizontal axis of the camera frame). Rather than actually producing a re-ordered hole list that is in horizontal position order, a computationally expensive task, pointers to the left and right holes may be added to the semantic description of a line. It may not be necessary to know the actual order of the holes between the two ends. Also (for display purposes in the realtime operator monitor) "left-endedness" and "right-endedness" may be added to the characteristics of the holes involved.

Pulse Spacing

Figure 11:
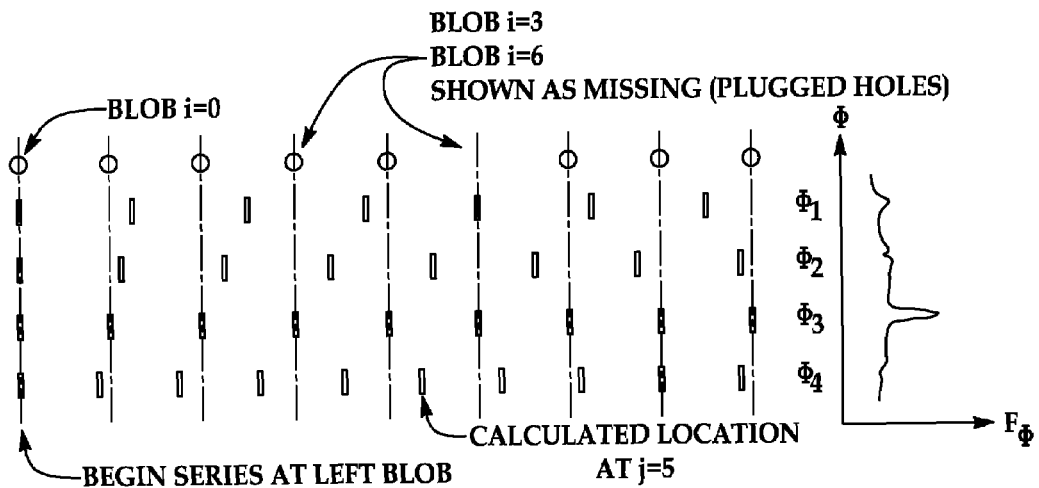
FIG. 11 is a method for measuring the spacing between holes along a line.

In block 710, the pulse frequency of the drilling laser, which in combination with the scan velocity of the laser optics, may set the spacing between holes along the scanning direction. In practice, this may be a very constant, well-controlled value. In keeping with the philosophy of this system, however, that rate from the geometry of the perforations in the image may be measured rather than simply making use of this a priori knowledge. FIG. 11 illustrates a method which may be used for measuring the spacing along a line.

Given a line, a set of candidate hole locations may be calculated given some spacing value, as shown. A calculation similar to what was used earlier to determine clustering along a projection line may be used to find the magnitude of the "force" between the actual hole locations and these candidate hole locations. The spacing may be varied (scanned) over a range and the resulting magnitude for each spacing value may be kept. When the scan is complete, a peak value may be present which represents the actual spacing of the holes along the line.

To limit the range of spacings scanned, the candidate distance may be varied from slightly less than the nearest neighbor distance to about 50% more than the average neighbor distance. It should be noted that the more obvious approach to this problem would be to simply calculate a Fourier transform of the locations, and look for the peak frequency in the resulting spectrum. However, the above method, given the known constraints on the range of expected spacings, may result in a faster computation. It may also be more robust in the presence of missing (plugged) holes, whereas a Fourier transform may leak significant energy into higher-frequency components, thus "washing out" the fundamental peak.

Identify Virtual Holes

In block 712, after a semantic representation of the hole array as a collection of lines across the image is obtained, it may be possible to go back through these lines to discover any missing (plugged) holes. This is perhaps the most important reason for building the line-by-line view. The knowledge of spacings and line arrangements may render it possible to identify the missing holes because there exists a geometric expectation of where they must be. A brute force method works well, and quickly: we align a comb of locations, at the detected spacing frequency, with the existing holes on a line. If no hole is near a given comb location, a virtual hole is simply added to the line at that location. The comb extends to the limits of the image, so it is possible that a new virtual hole will take on the identity of a line end, replacing the existing end.

Identify Cell Areas

Figure 12:
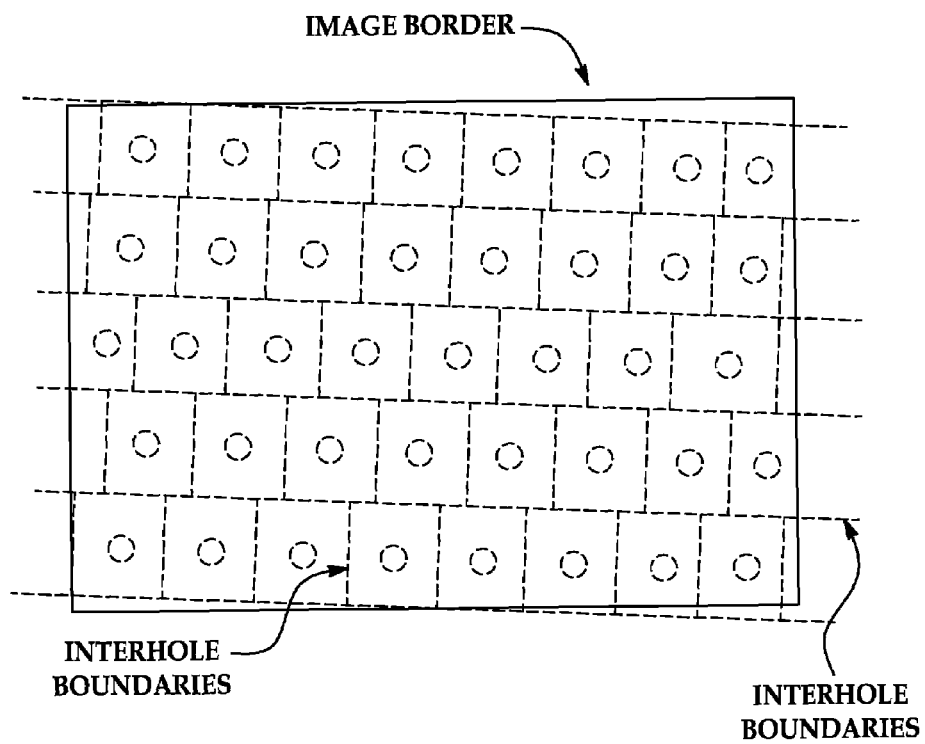
FIG. 12 is a graph which illustrates a geometric approach to determining the cell area of an hole.

After a complete semantic picture of an image is obtained, the next step may include determining the size of the actual area (cell) surrounding each hole in block 714. There may be many schemes which may be chosen to measure cell area, e.g. region-growing methods seeded with hole locations, but a simple geometric approach to save computation time may be used as illustrated in FIG. 12.

The entire image may be divided up according to straight line boundaries. First, the best-fit (linear regression) equation of a line may be determined for each semantic line (the holes along this line may "wobble" across it according to the degree of y-axis servo hunting mentioned hereinabove). These may be extended to the boundary of the image. Then, perpendicular line segments may be added midway between each hole, real or virtual. The outer boundary of a cell near an image edge may be presumed to be the same distance from the hole as the visible side, as shown in FIG. 12. For lines near the top and bottom of the image, the same philosophy may be applied, where a "virtual bounding line" is laid outside the actual image extent.

The area of each cell may simply be the geometric area of the quadrilateral surrounding each hole. This may be kept in "pixel space", or may be converted to square units of measure (e.g., square inches or square millimeters) if the sensor has been optically calibrated to determine the size of the image pixels. The cell area may be added as a characteristic of a hole.

Measure Total Optical Power

Figure 13:
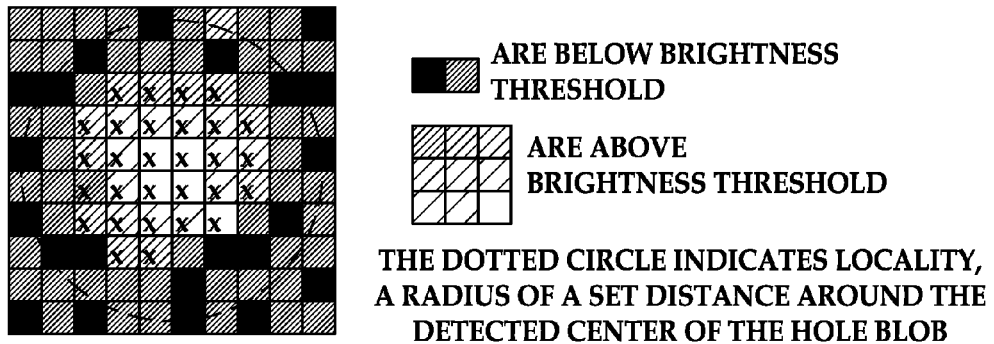
FIG. 13 is a graph which indicates measurement of the optical power at each hole location.

At this point in the method, a complete list of perforation locations, including those which appear to be plugged, has been obtained. In block 716, the optical power that is observed at each hole location may be measured. This may be a simple matter of going back to the original grayscale image and summing up the values of all pixels within a certain neighborhood of the hole center, and above a certain brightness level that is just above the background (unperforated) brightness. This is illustrated graphically in FIG. 13. The total optical power may be added as a characteristic to each hole description. Also, a rough estimate of hole diameter may be taken at this stage, as a simple template correlation of ideal circle diameter to the boundary pixels of the hole image.

It should be remembered that original segmentation of the image frame into blobs was dependent upon the binarization of the brightness according to some threshold. There may exist some holes which are partially plugged but show a brightness less than this threshold. Discovery of the location of virtual holes, however, may allow the inclusion of this small amount of gas flow through the hole even though it was originally undetectable. The concept of virtual holes may also allow inclusion of a zero-flow contribution to the total pressure drop to be mapped in a geometric distribution. This ability is a unique distinction that separates the method of this invention from conventional methods.

Assemble Image Statistics

Figure 14:
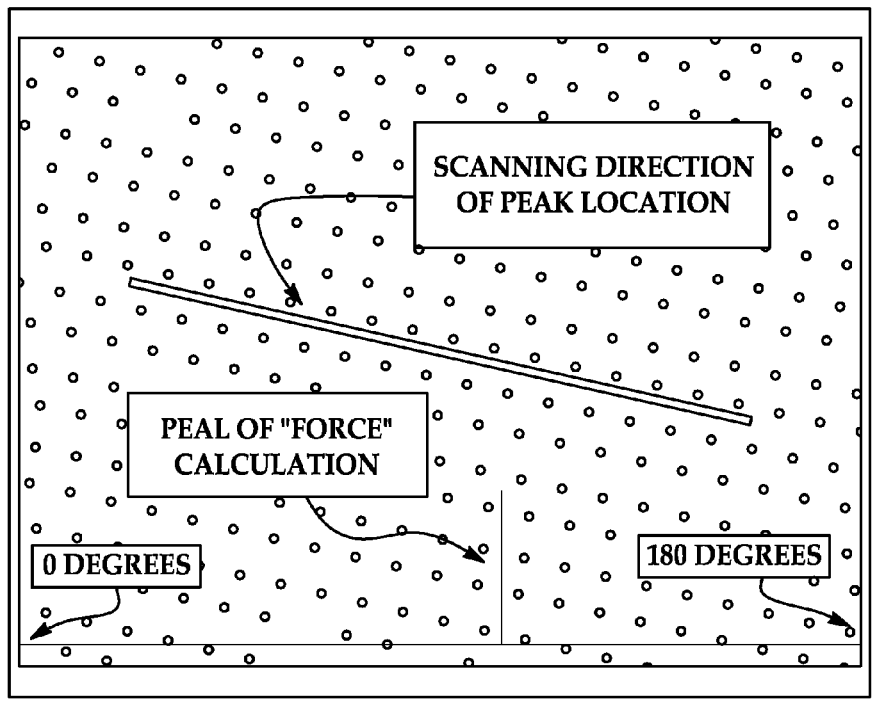
FIG. 14 illustrates key indicators of an algorithm-identified scanning angle.

The information that is assembled concerning a given image may vary according to the needs of the particular type of inspection being performed. However, the semantic line list, which points to all holes real and virtual within the image, may contain sufficient data to calculate any combination of the following:

- Y-axis servo hunting magnitude and variation
- Spacing magnitude and variation along scanning direction
- Interline spacing and distribution
- Optical porosity per unit area (relates to Pd)
- Variance of optical porosity within image
- Percentage of blocked holes and their geometric distribution
- Scanning direction (angle) relative to the sensor Format and Display Data for Operator The type of operator display that should be designed for the system 100 may vary depending on where in a factory the system 100 is deployed, and what characteristic is important at the time. For example, FIG. 14 illustrates a couple of key indicators for how the algorithms have identified the scanning angle. The green histogram-like plot across the bottom of the image shows the value of the "force" calculation for every angle from 0 to 180 degrees, and the green line on the display shows an operator how well the automated angle extraction agrees with what can be seen visually (in this example, perfectly).

Figure 15:
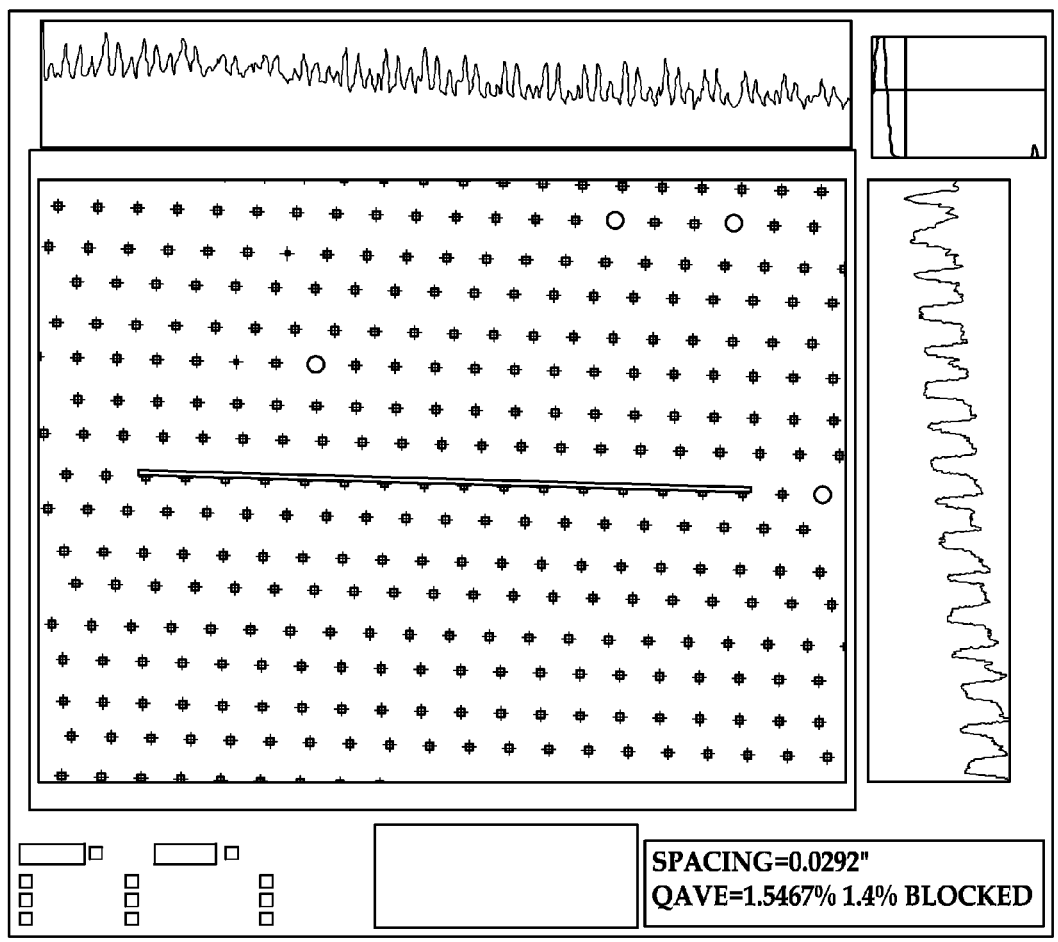
FIG. 15 is a general-purpose type of display which can be used to verify the correct operation of an entire algorithm suite at a glance.

FIG. 15 illustrates a more general-purpose type of display which can be used to verify the correct operation of the entire algorithm suite at a glance. Here, the optical porosity value for each hole is shown numerically. The center of each hole is indicated with a crosshair, virtual holes are covered with a circle, and line membership is shown by using an arbitrary false color for the hole crosshairs. The two displays above and to the right of the main image are the projected brightness histograms for each direction. A brightness histogram for the entire image is shown in the upper right corner, allowing an indication of how the automatic camera gain control filter algorithms are working. Many alternative types of realtime displays can be developed for the purpose.

Increment Sensor Scan Position and Repeat Until Finished

As alluded to herein above, the exact method of moving the sensor 122 with respect to the perforated panel 116 may be by moving the sensor 122, moving the panel 116, or a combination involving multiple fixed cameras 101 and a moving panel 116. Images may be taken while the relative motion is stopped, or they may be frozen by a short exposure time. There may also be a certain pre-programmed variation in the scanning technique to accommodate panels that are not rectangular. However the motion is accomplished, the image frame processing may continue until inspection of the entire panel 116 is completed.

Post-Processing

Figure 16:
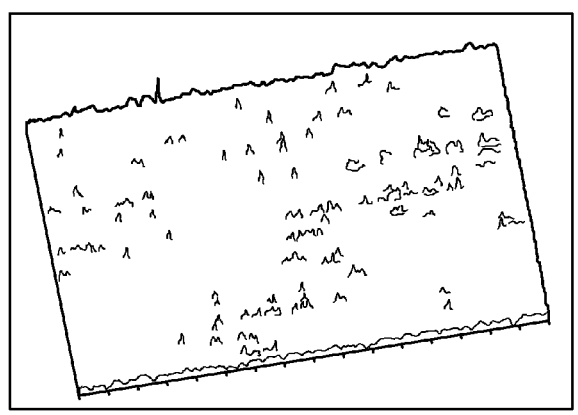
FIG. 16 illustrates a method of displaying a collection of individual images that have been mapped to an actual panel geometry.

The heart of the processing in the present disclosure is all of the activity that goes into analysis of a single image frame. However, to be useful in the manufacturing environment it may be necessary to assemble these frames together into a coherent view of the entire panel being measured. This can be done simply by keeping track of the location on the panel from where each image has been taken. The types of post-processing implemented may include but are not limited by the following operations:

- Correlation of individual image statistics to part geometry
- Creation and display of a false-color computer graphic overlay of Pd onto CAD part graphics
- Identification and display of regional compliance to design specification of hole diameter, spacing, and interline distance
- Recording of pertinent information for future reference and/or documentation FIG. 16 illustrates one method of displaying a collection of individual images that have been mapped to the actual panel geometry. Here, the optical power from each hole has been assigned a false color as well as a "height", and the result is shown as a three-dimensional map of the surface. In this way, areas which are deficient can be seen at a glance, and a numeric value quickly correlated to the problem.

Unload Panel from Apparatus

Finally, a means of easily unloading a perforated panel 116 from the system 100 under test must be provided. In the case of our proposed apparatus illustrated in FIGS. 5A and 5B, the panel may simply continue out the exit side of the machine. One can envision the inspection process as a simple station along a conveyor line. Other implementations, such as a step-and-repeat robotic gantry, may be used.

Figure 17:
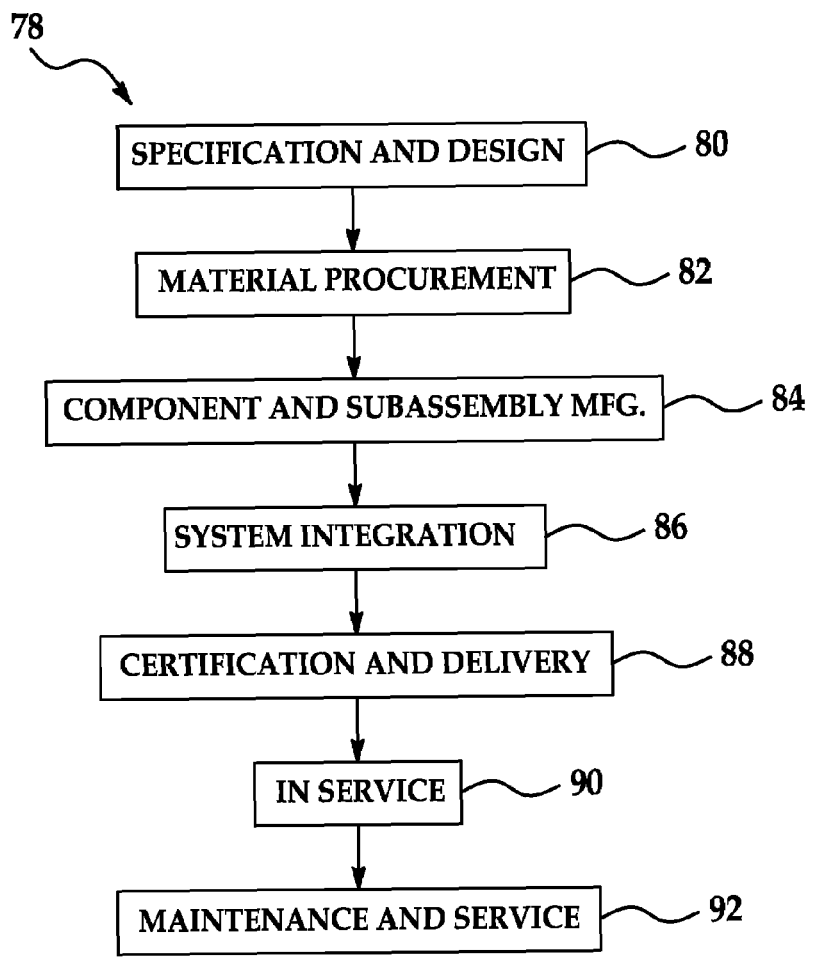
FIG. 17 is a flow diagram of an aircraft production and service methodology.
Figure 18:
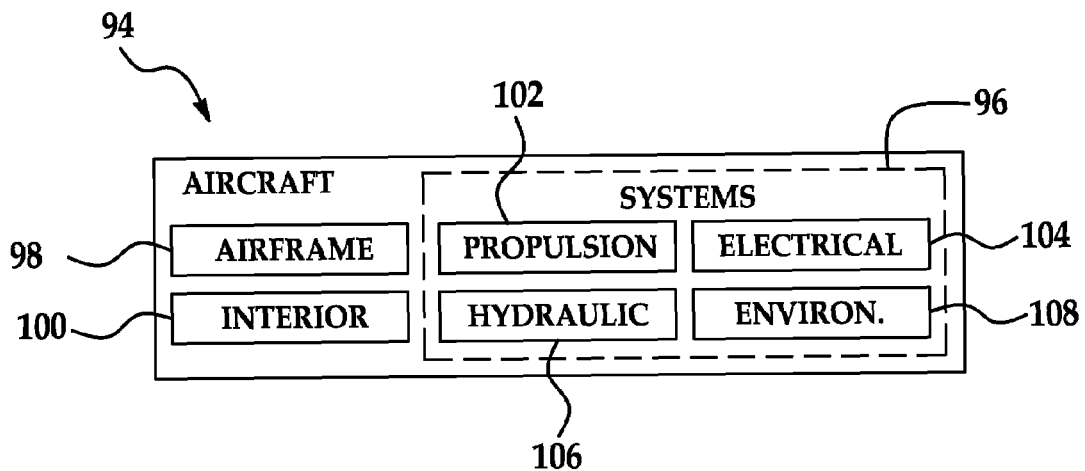
FIG. 18 is a block diagram of an aircraft.

Referring next to FIGS. 17 and 18, embodiments of the disclosure may be used in the context of an aircraft manufacturing and service method 78 as shown in FIG. 17 and an aircraft 94 as shown in FIG. 18. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 18, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A system for measurement of pressure drop through a perforated panel having panel holes, comprising:
   a sensor comprising:
     an illumination source adapted to illuminate the perforated panel;
     a lens spaced-apart with respect to said illumination source; and
     a camera interfacing with said lens; and
   a controller connected to said camera and adapted to receive image frames of the panel openings from said camera, measure an optical porosity of the perforated panel, identify a number and locations of missing and blocked panel holes in the perforated panel, determine a shape of a small region associated with each panel hole and calculate a pressure drop through the perforated panel based on the optical porosity of the perforated panel, the number and locations of the missing and blocked panel holes and the shape of the small region associated with each panel hole.

2. The system of claim 1 wherein said illumination source comprises a distributed light source.

3. The system of claim 1 wherein said lens comprises a telecentric lens.

4. The system of claim 1 wherein said sensor is adapted to move in a scanning motion with respect to the perforated panel.

5. The system of claim 1 wherein the perforated panel is adapted to move in a scanning motion with respect to said sensor.

6. The system of claim 1 wherein said sensor and the perforated panel are adapted to move in a scanning motion with respect to each other.

7. The system of claim 1 wherein said controller is adapted to display the pressure drop through the perforated panel in real time.

8. The system of claim 1 wherein said controller comprises:
   a blob detection component adapted to find locations of the panel holes in the perforated panel and use grayscale information to measure total optical power of light rays transmitted from said illumination source through the perforated panel;
   an optical porosity measurement component adapted to measure optical porosity by summing a pixel response in the local region of each of the panel holes;
   an image frame analyzing component adapted to analyze individual image frames from said camera and identify spacing and expected locations of the panel holes in the perforated panel;
   a small region measurement component adapted to utilize spacing and expected locations of the panel holes and measure the shape of a small region associated with each panel hole; and
   a pressure drop calculating component adapted to calculate and display a pressure drop over the perforated panel.

9. A method for measurement of pressure drop through a perforated panel having panel holes, comprising:
   loading a perforated panel having panel holes;
   executing a scan of said perforated panel by:
   illuminating said perforated panel; and
   capturing image frames of said panel holes in said perforated panel; and
   summarizing and archiving data by:
   measuring an optical porosity of said perforated panel;
   identifying a number and locations of missing and blocked panel holes in said perforated panel; and
   calculating a pressure drop through said perforated panel based on said optical porosity of said perforated panel and said number and locations of missing and blocked panel holes in said perforated panel.

10. The method of claim 9 further comprising determining a shape of a small region associated with each of said panel holes and wherein said calculating a pressure drop through the perforated panel comprises calculating a pressure drop through the perforated panel based on said optical porosity of said perforated panel, said number and locations of missing and blocked panel holes in said perforated panel and said shape of a small region associated with each of said panel holes.

11. The method of claim 9 wherein said illuminating said perforated panel comprises backlighting said perforated panel.

12. The method of claim 11 wherein said backlighting said perforated panel comprises providing a sensor having an illumination source, a lens disposed in spaced-apart relationship with respect to said illumination source and a camera interfacing with said lens and positioning said perforated panel between said illumination source and said camera.

13. The method of claim 12 wherein said capturing image frames of said panel holes in said perforated panel comprises moving said sensor in a scanning motion with respect to said perforated panel while rendering stationary said perforated panel.

14. The method of claim 12 wherein said capturing image frames of said panel holes in said perforated panel comprises rendering said sensor stationary while moving said perforated panel in a scanning motion with respect to said sensor.

15. The method of claim 12 wherein said capturing image frames of said panel holes in said perforated panel comprises moving said sensor in a scanning motion with respect to said perforated panel while moving said perforated panel in a scanning motion with respect to said sensor.

16. A method for measurement of pressure drop through a perforated panel having panel holes, comprising:
   loading a perforated panel into position for imaging;
   illuminating said perforated panel;
   capturing images of panel holes in said perforated panel;
   pre-processing said images;
   extracting metageometry of said panel holes;
   assembling image statistics based on said metageometry;
   determining a pressure drop through the perforated panel based on said image statistics; and
   formatting display data of said pressure drop.

17. The method of claim 16 wherein said pre-processing said images comprises extracting a list of blobs.

18. The method of claim 16 wherein said extracting metageometry of said panel holes comprises measuring a total optical power of each panel hole.

19. The method of claim 16 wherein said assembling image statistics comprises determining an optical porosity of said perforated panel per unit area.

20. The method of claim 16 wherein said assembling image statistics comprises determining a spacing magnitude and variation of said panel holes along a scanning direction and determining an interline spacing of said panel holes.

21. A system for measurement of pressure drop through a perforated panel having panel holes, comprising:
   a sensor adapted for moving in a scanning motion relative to the perforated panel and comprising:
     a distributed light illumination source adapted to backlight the perforated panel;
     a telecentric lens spaced-apart with respect to said illumination source; and a camera interfacing with said lens; and a controller connected to said camera and adapted to receive image frames of the panel openings from said camera, said controller comprising:

a blob detection component adapted to find locations of the panel holes in the perforated panel and use grayscale information to measure total optical power of light rays transmitted from said illumination source through the perforated panel;

an optical porosity measurement component adapted to measure optical porosity by summing a pixel response in the local region of each of the panel holes;

an image frame analyzing component adapted to analyze individual image frames from said camera and identify spacing and expected locations of the panel holes in the perforated panel;

a small region measurement component adapted to utilize spacing and expected locations of the panel holes and measure the shape of a small region associated with each panel hole; and a pressure drop calculating component adapted to calculate and display a pressure drop over the perforated panel.

22. A method for measurement of pressure drop through a perforated panel having panel holes, comprising:

loading a perforated panel into position for imaging;

backlighting said perforated panel with light rays from an illumination source;

capturing images of panel holes in said perforated panel;

pre-processing said images by acquiring said images, normalizing said images and updating camera controls and extracting a list of blobs;

extracting metageometry of said panel holes by obtaining a first approximation of hole spacing, identifying and measuring an angle of a scanning axis, identifying pulse spacing of panel openings along said scanning axis, locating a probable location of plugged holes in the perforated panel, constructing a semantic representation of an array of the panel holes in the perforated panel, identifying hole-local regions and measuring a total optical power of each panel hole;

assembling image statistics based on said metageometry by obtaining a Y-axis servo hunting magnitude and variation, obtaining a spacing magnitude and variation along said scanning direction, obtaining an interline spacing of the panel holes, obtaining an optical porosity of said perforated panel per unit area, obtaining a variance of optical porosity within said images, obtaining a percentage of blocked panel openings in said perforated panel and obtaining a scanning angle;

determining a pressure drop through the perforated panel based on said image statistics; and formatting display data of said pressure drop.

* * * * *